United States Patent
Samson, Jr.

(10) Patent No.: US 7,437,272 B2
(45) Date of Patent: Oct. 14, 2008

(54) SYSTEMS AND METHODS FOR SELF-SYNCHRONIZED DIGITAL SAMPLING

(75) Inventor: John R. Samson, Jr., Palm Harbor, FL (US)

(73) Assignee: Honeywell International Inc., Morristown, NJ (US)

( * ) Notice: Subject to any disclaimer, the term of this patent is extended or adjusted under 35 U.S.C. 154(b) by 386 days.

(21) Appl. No.: 11/264,566

(22) Filed: Nov. 1, 2005

(65) Prior Publication Data

US 2007/0095142 A1    May 3, 2007

(51) Int. Cl.
*G06F 11/00* (2006.01)
*G06F 15/00* (2006.01)
(52) U.S. Cl. .................. 702/183; 702/75; 702/145
(58) Field of Classification Search ............... 702/183
See application file for complete search history.

(56) References Cited

U.S. PATENT DOCUMENTS

| 4,181,962 | A * | 1/1980 | West et al. ................ 702/145 |
| 6,508,122 | B1 * | 1/2003 | McCall et al. ............ 73/504.12 |
| 6,934,665 | B2 * | 8/2005 | Rober ........................ 702/189 |
| 2003/0036878 | A1 * | 2/2003 | Saarinen et al. ............ 702/145 |
| 2004/0078159 | A1 * | 4/2004 | Rober ........................ 702/76 |

* cited by examiner

*Primary Examiner*—Michael P. Nghiem
*Assistant Examiner*—Cindy H Khuu
(74) *Attorney, Agent, or Firm*—Fogg & Powers LLC

(57) ABSTRACT

Systems and methods for self-synchronized data sampling are provided. In one embodiment, a system for capturing synchronous data samples is provided. The system includes an analog to digital converter adapted to capture signals from one or more sensors and convert the signals into a stream of digital data samples at a sampling frequency determined by a sampling control signal; and a synchronizer coupled to the analog to digital converter and adapted to receive a rotational frequency signal from a rotating machine, wherein the synchronizer is further adapted to generate the sampling control signal, and wherein the sampling control signal is based on the rotational frequency signal.

25 Claims, 2 Drawing Sheets

SYSTEMS AND METHODS FOR SELF-SYNCHRONIZED DIGITAL SAMPLING

GOVERNMENT LICENSE RIGHTS

Figure 1:
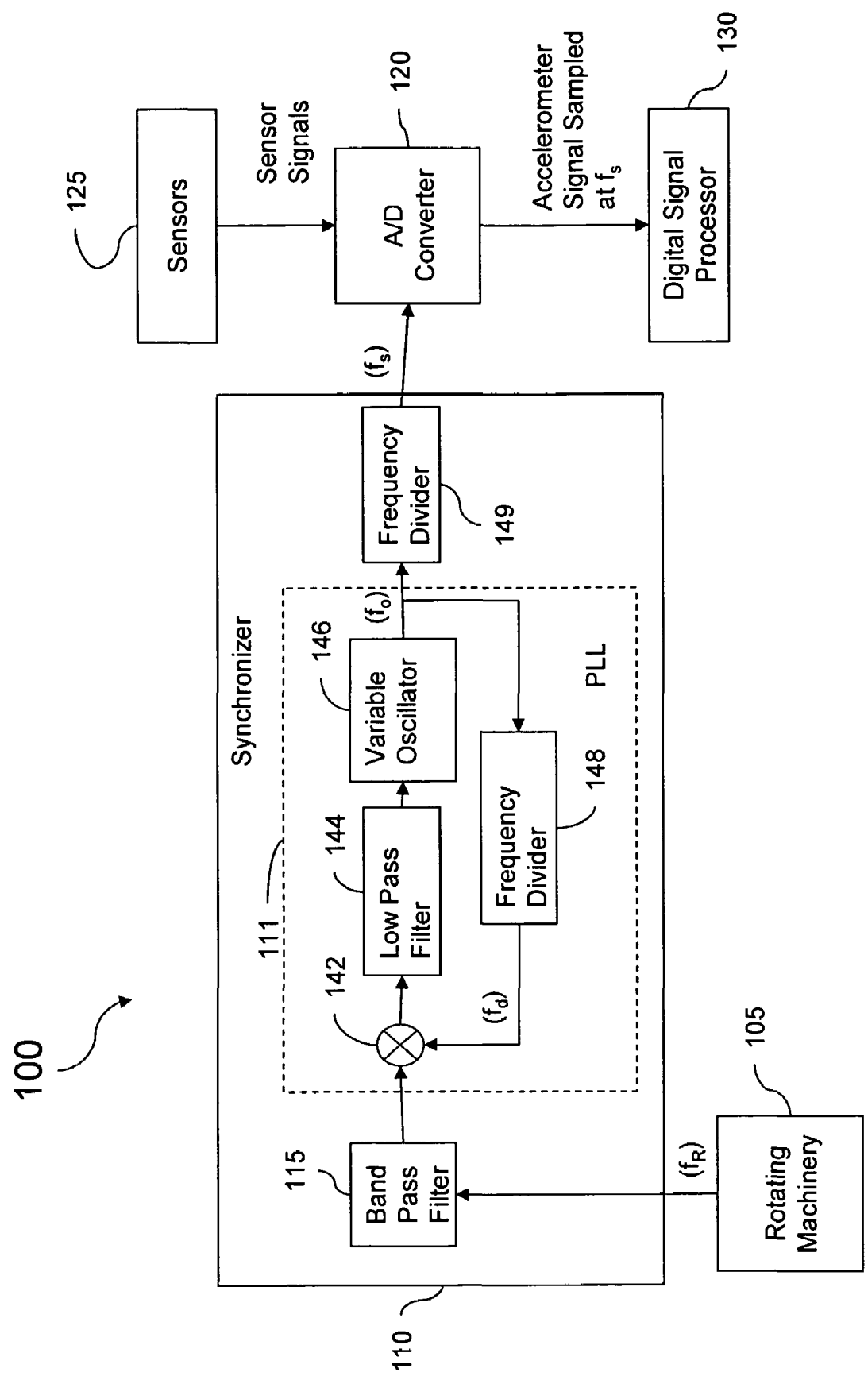

The U.S. Government may have certain rights in the present invention as provided for by the terms of Contract No. NAS8-01140 awarded by NASA.

TECHNICAL FIELD

The present invention generally relates to digital sampling and more particularly to capturing synchronous data samples.

BACKGROUND

Coherent Phase Line Enhancement (CPLE) is a technique for analyzing spectral characteristics of high speed rotating turbine machinery. The CPLE technique is employed because of its benefits for detecting synchronous and harmonic phenomena. For example, for the main engines of the Space Shuttle, accelerometers are used to sense vibration within pumps and turbines. Frequency analysis through fast Fourier transforms of the accelerometer data are used to detect, predict, and avoid potentially catastrophic engine failures. For example, vibrations within rotating machinery, occurring at first, second, third, or some other Nth harmonic of the rotational frequency can alone, or in combination, indicate current operating conditions within the machinery. These indications can further indicate the degradation of internal components, such as a bearing failure, which if left uncorrected, will result in further degradation or failure of the machinery. Therefore, when using CPLE, it is highly desirable to have to the accelerometer output sampled synchronously at a frequency which is proportional to the rotational speed of the rotating shaft, engine, pump, turbine or similar rotating machinery component.

Using techniques available in the art today, the sampling time of the accelerometer signal is estimated and the physically sampled data is interpolated back to desired synchronous sampling points to obtain a synchronous data set. Unfortunately, both the estimated synchronous sampling times and the data interpolation introduce errors into the analysis. In addition to producing errors, estimation of the sampling times and data interpolation functions also increase onboard data processing requirements. Further, problems with estimating shaft rotation and calculating interpolated accelerometer samples are exacerbated when the machinery is starting up and when the machinery is slowing down because the rotational speed of the machine is changing. For high speed rotating turbine machinery, start-up and slow-down are critical periods of operation for detecting, predicting, and avoiding failures. For performing an analysis such as CPLE, it is highly desirable to eliminate these sources of errors and the associated processing requirements.

For the reasons stated above and for other reasons stated below which will become apparent to those skilled in the art upon reading and understanding the specification, there is a need in the art for systems and methods for synchronizing digital sampling having reduced error levels compared to existing techniques.

SUMMARY

The Embodiments of the present invention provide methods and systems for self-synchronized digital sampling, and will be understood by reading and studying the following specification.

In one embodiment, a method for synchronous data frequency analysis is provided. The method comprises receiving a rotational frequency signal representing a rotational frequency of a rotating machine; generating a sampling control signal based on the rotational frequency signal; capturing one or more signals at a sampling frequency based on the sampling control signal to produce a sequence of synchronized data samples; and analyzing the sequence of synchronized data samples.

In another embodiment, a system for capturing synchronous data samples is provided. The system comprises an analog to digital converter adapted to capture signals from one or more sensors and convert the signals into a stream of digital data samples at a sampling frequency determined by a sampling control signal; and a synchronizer coupled to the analog to digital converter and adapted to receive a rotational frequency signal from a rotating machine, wherein the synchronizer is further adapted to generate the sampling control signal, and wherein the sampling control signal is based on the rotational frequency signal.

In yet another embodiment, a system for analyzing synchronous data is provided. The system comprises means for generating a sampling control signal based on a rotational frequency of a rotating machine; and means for converting one or more sensor signals into a sequence of data samples based on the sampling control signal, the means for converting responsive to the means for generating.

In still another embodiment, a computer-readable medium having computer-executable instructions for performing a method for synchronous data frequency analysis is provided. The method comprises receiving a rotational frequency signal representing a rotational frequency of a rotating machine; and generating a sampling control signal based on the rotational frequency signal.

DRAWINGS

Figure 2:
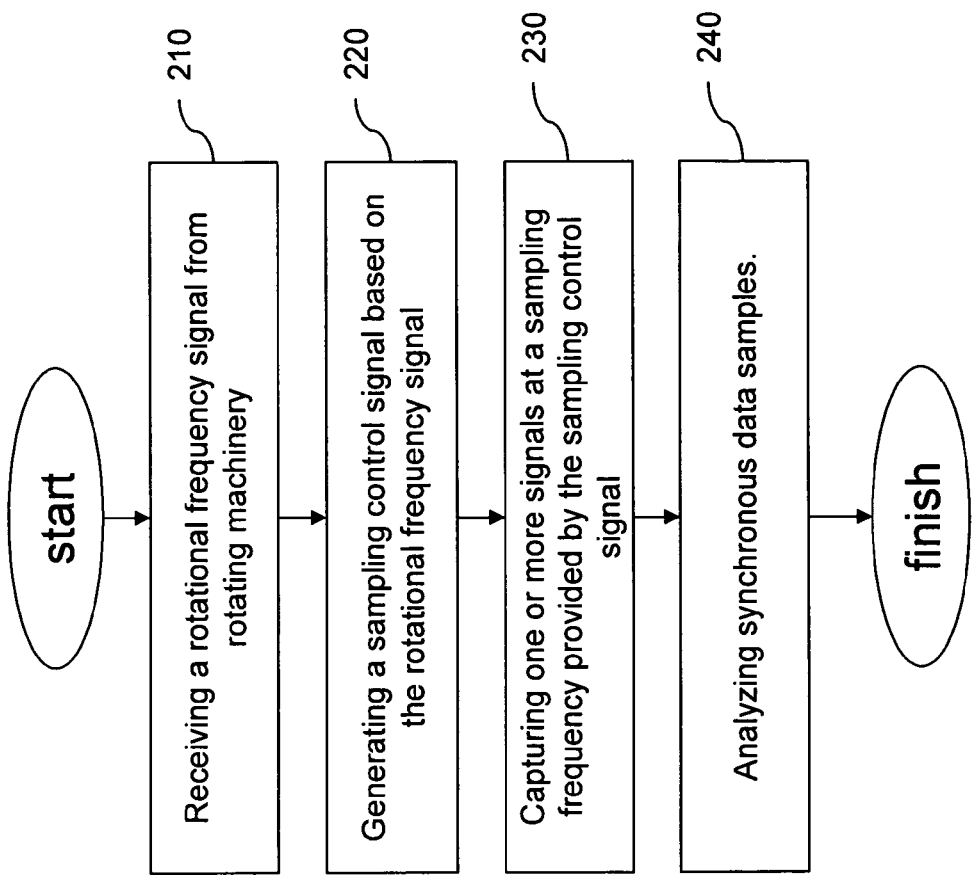

Embodiments of the present invention can be more easily understood and further advantages and uses thereof more readily apparent, when considered in view of the description of the preferred embodiments and the following figures in which:

FIG. 1 is a block diagram illustrating a system for capturing synchronous data samples of one embodiment of the present invention; and FIG. 2 is a flow chart illustrating a method for capturing and analyzing synchronous data samples of one embodiment of the present invention.

In accordance with common practice, the various described features are not drawn to scale but are drawn to emphasize features relevant to the present invention. Reference characters denote like elements throughout figures and text.

DETAILED DESCRIPTION

In the following detailed description, reference is made to the accompanying drawings that form a part hereof, and in which is shown by way of specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the scope of the present invention. The following detailed description is, therefore, not to be taken in a limiting sense.

Embodiments of the present invention address the problems associated with performing vibration analysis for rotating machinery by directly and dynamically coordinating data sample capture rates with the rotation of the machinery rather than using interpolated data samples having an estimated synchronization. Coordinating the capture of data samples with the rotation of machinery produces data for performing frequency analysis that is necessarily synchronous with the rotational frequency of the machinery.

FIG. 1 illustrates a system 100 for capturing synchronous data samples, of one embodiment of the present invention. System 100 supports CPLE processing and analysis without requiring estimation of sampling times and interpolation of data incurring the associated ambiguities and errors. System 100 comprises a synchronizer 110 and an analog to digital (A/D) converter 120. Synchronizer 110 receives a rotational frequency signal, from rotational machinery 105, that provides the rotational speed of rotational machinery 105. In one embodiment, rotational machinery 105 comprises one of, but not limited to, a pump, a turbine, or the like, having a rotating element, such as but not limited to, a shaft. In one embodiment, the rotational frequency signal is a waveform whose frequency components are proportional to the rotational speed of rotational machinery 105. In one embodiment, the signal waveform is one of either a continuous signal or a series of pulses having a fundamental period that is proportional to the rotational speed of rotational machinery 105. In one embodiment, the rotational frequency signal is a voltage signal having a frequency proportional to the rotational speed of rotational machinery 105. In one embodiment, A/D converter 120 is coupled to synchronizer 110 and coupled to receive analog signals from one or more sensors 125. In one embodiment, one or more sensors 125 comprise one or more accelerometers. A/D converter 120 outputs digital samples of the analog signals to digital signal processor 130.

In one embodiment, in operation, synchronizer 110 inputs the rotational frequency signal from rotational machinery 105 and based on the rotational frequency signal determines the rotational frequency of rotational machinery 105. In one embodiment, the rotational frequency signal provides a frequency ($f_R$) proportional the rotational speed of rotational machinery 105. In one embodiment, $f_R$ provides the rotational speed of rotational machinery 105 (i.e., $f=\omega/2\pi$, where $\omega$ is the angular rotational frequency of rotational machinery 105) multiplied by a constant ($N_1$). In one embodiment, $N_1$ is an integer constant. For example, in one embodiment, a fuel pump shaft produces a rotational frequency signal having eight pulses for each rotation of the shaft. In that case, $N_1$ is equal to eight. From $f_R$, synchronizer 110 determines a sampling frequency ($f_S$), proportional to $f_R$, for sampling data from the one or more sensors 125. In one embodiment, A/D converter 120 receives analog signals from one or more sensors 125, samples the analog signals at the sampling frequency $f_S$ determined by synchronizer 110, and outputs a sequence of synchronous digital samples to digital signal processor 130. In one embodiment, $f_S$ is equal to $f_R$ multiplied by a constant ($N_2$). In one embodiment, $N_2$ is an integer constant.

In one embodiment, synchronizer 110 further comprises a phase-lock loop (PLL) 111 configured to generate a sampling control signal to an A/D converter 120. In one embodiment, PLL 111 comprises a multiplier 142, a low pass filter 144, a variable oscillator 146, and a frequency divider 148. In one embodiment variable oscillator 146 is a voltage controlled oscillator.

In one embodiment, in operation, multiplier 142 multiplies the incoming signal $f_R$ from rotational machinery 105 with a frequency-divided output of variable oscillator 146. In one embodiment, multiplying $f_R$ with the frequency-divided output of variable oscillator 146 produces a signal having an upper and lower sideband. In one embodiment, low pass filter 144 receives the output from multiplier 142 and passes only the lower sideband to variable oscillator 146. Variable oscillator 146 then outputs a sampling control signal.

In one embodiment, sampling frequency $f_S$, used by A/D converter 120 to sample the output of the one or more sensors 125, is thus equal to the frequency ($f_o$) of the sampling control signal output from variable oscillator 146. Frequency divider 148 closes the loop of PLL 111 by frequency dividing the output of variable oscillator 146 to match the fundamental input frequency $f_R$ coming from rotating machinery 105. In one embodiment, frequency divider 148 provides a frequency-divided output of variable oscillator 146 to multiplier 142. In one embodiment, the frequency-divided output of variable oscillator 146 is equal to the output of variable oscillator 146 divided by the product of constants $N_1$, and $N_2$ (i.e., $f_d=f_o/(N_1 \times N_2)$). The PLL formed by multiplier 142, low pass filter 144, variable oscillator 146, and frequency divider 148 causes the output of variable oscillator 146 and, correspondingly, sampling frequency $f_S$ to track the input signal $f_R$ from rotational machinery 105, resulting in synchronized sampling of accelerometer 125 signals.

As would be appreciated by one skilled in the art upon reading this specification, sampling frequency $f_S$, must satisfy the minimum Nyquist rate to avoid aliasing. Accordingly, in one embodiment sampling frequency $f_S$, is greater than f by at least the Nyquist rate (e.g. $f_S$, $\geq 2f$). To reduce the oversampling which can occur when sampling frequency $f_S$ is equal to variable oscillator 146's output frequency ($f_o$), in one embodiment, synchronizer 100 further comprises an optional second frequency divider 149 to reduce the sampling frequency $f_S$, to a desired rate that meets the minimum Nyquist rate. In one embodiment, second frequency divider 149 reduces sampling frequency $f_S$, by a factor of $N_3$ (i.e., $f_S$, = ($f_o/N_3$), where $N_3$ is selected to reduce $f_S$, to a frequency that meets the minimum Nyquist rate.

As described above, PLL 111 locks onto $f_R$ and tracks $f_R$ as rotational machinery 105 speeds up or slows down. In some applications, such as when an engine is starting and thus is rotating at considerably less than its normal operating speed, it is not necessarily desirable to sample sensor output at corresponding low sampling frequencies. Such applications are addressed by embodiments of the present invention as discussed below.

In one embodiment, when variable oscillator 146 senses the absence of an input signal, variable oscillator 146 becomes a free-running oscillator that results in a sampling control signal to A/D converter 120 having a nominal frequency, $f_{Snominal}$, sufficient to satisfy frequency analysis resolution requirements and the minimum Nyquist rate. In one embodiment, $f_{Snominal}$ is set to an expected value of $f_S$ for a normally operating machine. Examples of when an input signal is not produced include when rotational machinery 105 is not rotating. In one embodiment, the input signal from rotating machinery 105 is also filtered through a bandpass filter 115 prior to PLL 111. Bandpass filter 115 serves two purposes. First, the high end of bandpass filter 115 removes higher harmonics from the input signal, allowing only signals with frequencies less than or equal to $f_R$ to pass. Filtering higher harmonics ensures that PLL 111 locks onto $f_R$ rather than some other harmonic within the input signal. Second, in one embodiment, the low end of bandpass filter 115 removes noise and signals whose frequencies are less than those produced by rotating machinery 105 during operation. For example, in one embodiment, bandpass filter 115 blocks the input signal from rotational machinery 105 when rotational machinery 105 is rotating at significantly less than operating speed. This would most frequently occur when rotational machinery 105 has just started and is accelerating up to operating speed, or when machinery 105 has been turned off and is decelerating down to rest speed. During these periods, as described above, variable oscillator 146 outputs a nominal frequency, $f_{S_{nominal}}$, to A/D converter 120. Providing a nominal frequency sampling control signal to A/D converter 120 allows system 100 to continue to monitor for vibrations using a sampling frequency sufficient to satisfy frequency analysis resolution requirements and the minimum Nyquist rate, when rotational machinery 105 is running at significantly less than operation speed. In the case of a space shuttle engine, this allows vibration sensing and analysis prior to engine start and after engine shutdown to detect "popping" explosions cause by the igniting of leaked or unburned Oxygen.

As previously discussed, embodiments of the present invention provided synchronous data samples for performing frequency analysis of high speed rotating turbine machinery by directly coordinating the capture of accelerometer data samples with the rotation of the machinery under analysis. As would be appreciated by one skilled in the art, CPLE is one example of such a technique for analyzing the spectral characteristics of high speed rotating turbine machinery. FIG. 2 is a flow chart illustrating a method of synchronous data frequency analysis of one embodiment of the present invention. The method starts at 210 with receiving a rotational frequency signal from of a piece of rotational machinery. In one embodiment, the rotational machinery produces and outputs the rotational frequency signal as a sequence of one or more pulses for each rotation of a shaft within the rotational machinery. In one embodiment, the rotational machinery outputs $N_1$ pulses for each revolution of the shaft. In one embodiment, receiving a rotational frequency includes receiving the sequence of one or more pulses where the speed of the shaft is represented by the period of, or the timing between pulses. The method then proceeds to 220 with generating a sampling control signal. In one embodiment, the sampling control signal provides a sampling frequency that is proportional to the rotational frequency of the rotating machinery. In one embodiment, the sampling control signal is a voltage signal having a frequency equal to the rotational frequency multiplied by a constant, $N_2$. One skilled in the art upon reading this specification would appreciate that a value for $N_2$ is readily determined based on the resolution requirements of the particular frequency analysis being performed, and satisfying the minimum Nyquist rate.

In one embodiment, generating a sampling control signal is accomplished by providing the rotational frequency signal from the rotating machine to the input of a phase locked loop and outputting the sampling control signal from the phase locked loop. In one embodiment, where the phase locked loop comprises a multiplier, a variable oscillator, and a frequency divider, the method further comprises multiplying the rotational frequency signal with a frequency-divided output of the variable oscillator. The frequency of the variable oscillator output is then varied based on this product. In one embodiment, the frequency of the variable oscillator output is set to a nominal frequency in the absence of a rotational frequency signal. In one embodiment, the frequency of the variable oscillator output is set to the nominal frequency when the rotational frequency signal indicates that the rotating machine is operating at significantly less than its normal operating speed.

The method next continues to 230 with capturing one or more signals at a frequency equal to the sampling frequency. In one embodiment, capturing one or more signals comprises driving an A/D converter to capture the one or more signals at the sampling frequency. In one embodiment, capturing one or more signals comprises producing a sequence of synchronous data samples based on the one or more signals. In one embodiment, the one or more signals are produced by one or more sensors. In one embodiment, the one or more sensors comprise one or more accelerometers. In one embodiment, the one or more signals are produced by one or more accelerometers located on the rotating machinery. By capturing signals at the sampling frequency, the data samples captured from the signals are thus synchronous with the rotational frequency of the rotating machinery. In one embodiment, the method proceeds to 240 with analyzing the synchronous data samples. The output of the A/D converter is a stream of data samples that are synchronous with the rotation of the rotating machinery, thus allowing direct analysis of the data in the frequency domain, without requiring re-sampling of the data (i.e. estimating sampling times and interpolating sensor signal data to calculate a synchronous data set) and without incurring the associated calculation time, ambiguities and errors. Vibrations within the rotating machinery, occurring at a first, second, third, or some other Nth harmonic of the rotational frequency either alone, or in combination are readily correlated with an FFT of the synchronous data samples with knowledge of constants $N_1$ and $N_2$ by one skilled in the art upon studying this specification.

Several means are available to implement the synchronizer discussed above. These means include, but are not limited to, digital computer systems, programmable controllers, or field programmable gate arrays. Therefore other embodiments of the present invention are program instructions resident on computer readable media which when implemented by such processors, enable the processors to implement embodiments of the present invention. Computer readable media include any form of computer memory, including but not limited to punch cards, magnetic disk or tape, any optical data storage system, flash read only memory (ROM), non-volatile ROM, programmable ROM (PROM), erasable-programmable ROM (E-PROM), random access memory (RAM), or any other form of permanent, semi-permanent, or temporary memory storage system or device. Program instructions include, but are not limited to computer-executable instructions executed by computer system processors and hardware description languages such as Very High Speed Integrated Circuit (VHSIC) Hardware Description Language (VHDL).

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

What is claimed is:

1. A method for synchronous data frequency analysis, the method comprising:
  receiving a rotational frequency signal representing a rotational frequency of a rotating machine;
  generating a sampling control signal based on the rotational frequency signal;
  capturing one or more signals at a sampling frequency based on the sampling control signal to produce a sequence of synchronized data samples; and
  analyzing the sequence of synchronized data samples;

wherein when the rotational frequency indicates the rotating machine is operating at a normal operating speed, the sampling frequency is proportional to the rotational frequency of the rotating machine; and wherein when the rotational frequency indicates the rotating machine is operating at below the normal operating speed, the sampling frequency is equal to a nominal sampling frequency.

2. The method of claim 1 further comprising:
generating the one or more signals from one or more accelerometers located on the rotating machine.

3. The method of claim 1 further comprising:
generating the one or more signals from one or more sensors.

4. The method of claim 1 further comprising:
analyzing a Fourier transform of the sequence of synchronized data samples.

5. The method of claim 1, wherein the sampling frequency is proportional to the rotational frequency of the rotating machine.

6. The method of claim 5, wherein the sampling frequency is proportioned to satisfy a Nyquist rate with respect to the rotational frequency of the rotating machine.

7. The method of claim 1 further comprising:
filtering the rotational frequency signal, wherein harmonics greater than a fundamental harmonic are removed from the rotational frequency signal.

8. The method of claim 1 further comprising:
filtering the rotational frequency signal, wherein harmonics less than a fundamental harmonic produced by the rotating machine when the rotating machine is running at a normal operating speed are removed from the rotational frequency signal.

9. The method of claim 1, wherein generating a sampling control signal further comprises:
receiving the rotational frequency signal with a phase locked loop; and
outputting the sampling control signal from the phase locked loop.

10. A system for capturing synchronous data samples, the system comprising:
an analog to digital converter adapted to capture signals from one or more sensors and convert the signals into a stream of digital data samples at a sampling frequency determined by a sampling control signal; and
a synchronizer coupled to the analog to digital converter and adapted to receive a rotational frequency signal from a rotating machine, wherein the synchronizer is further adapted to generate the sampling control signal, and wherein the sampling control signal is based on the rotational frequency signal, the synchronizer comprising:
a phase lock loop circuit adapted to input the rotational frequency signal and output the sampling control signal, wherein the sampling control signal is synchronized with the rotational frequency signal, the phase lock loop circuit comprising:
a variable oscillator coupled to the analog to digital converter and adapted to output the sampling control signal;
a first frequency divider adapted to output a first signal representing the frequency of the sampling control signal divided by a constant; and
a multiplier adapted to multiply the rotational frequency signal with the first signal;

wherein the variable oscillator varies a frequency of the sampling control signal based on a product of the rotational frequency signal and the first signal.

11. The system of claim 10, wherein the synchronizer generates a sampling control signal that results in the sampling frequency being proportional to a rotational frequency of the rotating machine.

12. The system of claim 11, wherein the synchronizer generates a sampling control signal that results in the sampling frequency satisfying a minimum Nyquist rate with respect to the rotational frequency of the rotating machine.

13. The system of claim 10, the synchronizer further comprising:
a second frequency divider adapted to input the sampling control signal from the variable oscillator and reduce the sampling frequency of the sampling control signal by a constant.

14. The system of claim 10, further comprising:
a low pass filter adapted to filter the product of the rotational frequency signal and the first signal and communicate a second signal to the variable oscillator based on the product of the rotational frequency signal and the first signal; and
wherein the variable oscillator varies a frequency of the sampling control signal based on the second signal.

15. The system of claim 14, wherein the low pass filter communicates only a lower sideband of the product of the rotational frequency signal and the first signal to the variable oscillator.

16. The system of claim 10 further comprising:
a bandpass filter adapted to filter from the rotational frequency signal harmonics less than a fundamental harmonic produced when the rotating machine is running at a normal operating speed; and
wherein the bandpass filter is further adapted to filter from the rotational frequency signal harmonics greater than the fundamental harmonic.

17. The system of claim 10, wherein when the rotational frequency signal indicates the rotating machine is operating at a normal operating speed, the synchronizer generates a sampling control signal that results in the sampling frequency being based on a rotational frequency of the rotating machine; and
when the rotational frequency signal indicates the rotating machine is operating at less than normal operating speed, the synchronizer generates a sampling control signal that results in the sampling frequency being equal to a nominal sampling frequency.

18. The system of claim 10 further comprising:
a digital signal processor adapted to input the stream of digital data samples and perform one or more frequency analyses based on the stream of digital data samples.

19. A system for analyzing synchronous data, the system comprising:
means for generating a sampling control signal based on a rotational frequency of a rotating machine; and
means for converting one or more sensor signals into a sequence of data samples based on the sampling control signal, the means for converting responsive to the means for generating;
wherein when a rotational frequency signal indicates the rotating machine is operating at a normal operating speed, a sampling control signal is generated that results in a sampling frequency being based on the rotational frequency of the rotating machine; and
wherein when the rotational frequency signal indicates the rotating machine is operating at less than normal operating speed, a sampling control signal is generated that results in the sampling frequency being equal to a nominal sampling frequency.

20. The system of claim 19 further comprising:
means for analyzing the sequence of data samples.

21. The system of claim 19, wherein the means for generating a sampling control signal generates a sampling control signal comprising a sampling frequency that is proportional to the rotational frequency of the rotating machine.

22. The system of claim 21, wherein the means for generating a sampling control signal generates a sampling control signal comprising a sampling frequency satisfying a minimum Nyquist rate with respect to the rotational frequency of the rotating machine.

23. A computer-readable medium having computer-executable instructions for performing a method for synchronous data frequency analysis, the method comprising:
receiving a rotational frequency signal representing a rotational frequency of a rotating machine; and
generating a sampling control signal based on the rotational frequency signal;
wherein when the rotational frequency indicates the rotating machine is operating at a normal operating speed, a sampling frequency is proportional to the rotational frequency of the rotating machine; and
wherein when the rotational frequency indicates the rotating machine is operating at below the normal operating speed, the sampling frequency is equal to a nominal sampling frequency.

24. The computer-readable medium of claim 23, wherein the method further comprises:
capturing one or more signals at a sampling frequency based on the sampling control signal to produce a sequence of synchronized data samples.

25. The computer-readable medium of claim 24, wherein the method further comprises:
analyzing a Fourier transform of the sequence of synchronized data samples.

* * * * *